United States Patent
Oster et al.

(10) Patent No.: US 10,729,920 B2
(45) Date of Patent: Aug. 4, 2020

(54) SYSTEMS AND METHODS FOR QUANTIFYING RADIATION BEAM CONFORMITY

(71) Applicant: Varian Medical Systems International AG, Cham (CH)

(72) Inventors: Matthias Oster, Palo Alto, CA (US); Andres Graf, Oberwil (CH)

(73) Assignee: Varian Medical Systems International AG (CH)

(*) Notice: Subject to any disclaimer, the term of this patent is extended or adjusted under 35 U.S.C. 154(b) by 117 days.

(21) Appl. No.: 14/873,457

(22) Filed: Oct. 2, 2015

(65) Prior Publication Data

US 2017/0095678 A1    Apr. 6, 2017

(51) Int. Cl.
*A61N 5/10* (2006.01)

(52) U.S. Cl.
CPC ......... *A61N 5/1071* (2013.01); *A61N 5/1036* (2013.01); *A61N 5/1045* (2013.01); *A61N 5/1067* (2013.01); *A61N 5/1075* (2013.01); *A61N 5/1037* (2013.01); *A61N 5/1038* (2013.01); *A61N 2005/1057* (2013.01); *A61N 2005/1074* (2013.01)

(58) Field of Classification Search
CPC .. A61N 5/1049; A61N 5/1067; A61N 5/1037; A61N 5/1045; A61N 5/1075; A61N 5/107; A61N 5/1071; A61N 5/103; A61N 5/1064; A61N 5/1048; A61N 5/1036
USPC ..................................................... 250/252.1
See application file for complete search history.

(56) References Cited

U.S. PATENT DOCUMENTS

| | | | | |
|---|---|---|---|---|
| 2003/0201403 A1* | 10/2003 | Svatos | ............ | A61N 5/1049 250/505.1 |
| 2004/0071261 A1* | 4/2004 | Earl | ............ | A61N 5/1031 378/65 |
| 2005/0123098 A1* | 6/2005 | Wang | ............ | A61N 5/1031 378/151 |
| 2006/0020195 A1* | 1/2006 | Falco | ............ | A61N 5/1049 600/407 |
| 2006/0045238 A1* | 3/2006 | Nguyen | ............ | A61N 5/103 378/65 |

(Continued)

OTHER PUBLICATIONS

Lomax, N.J., et al., "Quantifying the Degree of Conformity in Radiosurgery Treatment Planning" Int. J. Radiation Oncology Biol. Phys., vol. 55, No. 5, pp. 1409-1419, copyright 2003.

(Continued)

*Primary Examiner* — Taeho Jo
(74) *Attorney, Agent, or Firm* — Vista IP Law Group, LLP

(57) ABSTRACT

A method for quantifying radiation beam conformity includes: obtaining first information regarding a prescribed aperture; obtaining second information regarding an actual aperture defined by components of a collimator; and determining, using a processing unit, a metric based on the first information regarding the prescribed aperture and the second information regarding the actual aperture, wherein the metric indicates an amount of over-exposed aperture area, an amount of under-exposed aperture area, or both, and wherein the processing unit comprises one or more input for receiving the first and second information, and comprises a metric determination module configured to determine the metric based on the first information and the second information.

28 Claims, 5 Drawing Sheets

(56) References Cited

U.S. PATENT DOCUMENTS

| | | | | |
|---|---|---|---|---|
| 2007/0041497 A1* | 2/2007 | Schnarr | A61N 5/103 | 378/65 |
| 2007/0053492 A1* | 3/2007 | Kidani | A61B 6/463 | 378/65 |
| 2007/0211939 A1* | 9/2007 | Kaus | A61B 6/00 | 382/173 |
| 2008/0002811 A1* | 1/2008 | Allison | A61N 5/103 | 378/65 |
| 2008/0011945 A1* | 1/2008 | Maurer, Jr. | A61N 5/103 | 250/252.1 |
| 2008/0123813 A1* | 5/2008 | Maurer | A61N 5/103 | 378/96 |
| 2008/0159478 A1* | 7/2008 | Keall | A61N 5/1042 | 378/65 |
| 2010/0012829 A1* | 1/2010 | Islam | A61N 5/1048 | 250/252.1 |
| 2010/0034357 A1* | 2/2010 | Svesson | A61N 5/1042 | 378/152 |
| 2010/0046713 A1* | 2/2010 | Nord | A61N 5/1042 | 378/125 |
| 2010/0171964 A1* | 7/2010 | Matsinos | A61N 5/1031 | 356/610 |
| 2010/0177870 A1* | 7/2010 | Nord | A61N 5/103 | 378/65 |
| 2010/0268073 A1* | 10/2010 | Falco | A61N 5/1049 | 600/427 |
| 2012/0053961 A1* | 3/2012 | Wang | G06Q 50/22 | 705/2 |
| 2012/0099704 A1* | 4/2012 | Ruan | A61N 5/1031 | 378/65 |
| 2012/0184841 A1* | 7/2012 | Nielsen | A61N 5/1039 | 600/411 |
| 2012/0256103 A1* | 10/2012 | Luzzara | A61N 5/1045 | 250/492.1 |
| 2013/0023718 A1* | 1/2013 | Nord | A61N 5/1036 | 600/1 |
| 2013/0216026 A1* | 8/2013 | Nord | A61N 5/1037 | 378/65 |
| 2014/0031603 A1* | 1/2014 | Robar | A61N 5/1049 | 600/1 |
| 2014/0263990 A1* | 9/2014 | Kawrykow | A61N 5/1031 | 250/252.1 |
| 2015/0045604 A1* | 2/2015 | Sawkey | A61N 5/1068 | 600/1 |
| 2015/0051434 A1* | 2/2015 | Kumar | A61N 5/1039 | 600/1 |
| 2015/0087879 A1* | 3/2015 | Nelms | A61N 5/103 | 600/1 |
| 2015/0124930 A1* | 5/2015 | Verhaegen | A61N 5/1047 | 378/62 |
| 2015/0314140 A1* | 11/2015 | Verhaegen | A61N 5/1047 | 378/62 |
| 2016/0287906 A1* | 10/2016 | Nord | A61N 5/1071 | |
| 2017/0050051 A1* | 2/2017 | Berbeci | A61B 5/05 | |

OTHER PUBLICATIONS

Ceberg, S., "3D Verification of Dynamic and Breathing Adapted Radiotherapy using Polymer Gel Dosimetry" Medical Radiation Physics Department of Clinical Sciences, Malmö Lund University, 2010, 136 pages.

* cited by examiner

SYSTEMS AND METHODS FOR QUANTIFYING RADIATION BEAM CONFORMITY

FIELD

The field of the application relates to medical procedures involving use of radiation, and more particularly, to systems and methods for quantifying radiation beam conformity.

BACKGROUND

Radiation therapy involves medical procedures that selectively expose certain areas of a human body, such as cancerous tumors, to high doses of radiation. Radiation may also be used to obtain images of the patient during an imaging procedure.

The goal of radiation treatment delivery is to deliver the prescribed dose of the treatment plan as precise as possible, i.e., following the planned volumetric dose distributions to both the target (e.g., tumor) as well as the surroundings (e.g., organs at risk). This is commonly known as "conformity" and is one of the parameters in treatment planning.

During treatment delivery, this conformity is currently not systematically quantified. Instead, single axis deviation limits are evaluated, which specifies tolerances for the position of any moving axis, such as the gantry rotation or a leaf of a multi-leaf collimator. These single axis limits do not quantify deviation of several axes. In particular, they do not quantify deviation of several axes but still below the limit— e.g., a single multi-leaf collimator (MLC) leaf might stop the treatment by exceeding the tolerance, while the treatment would not have been stopped if all MLC leaves are offset by just less than the limit. Also, these single axis limits may not be clinically relevant. For example, a couch axis deviation in the direction along the treatment beam may not have significant impact on the treatment delivery since the difference in the depth dose resulting from such deviation would be marginal. However, the same couch axis deviation may have a larger dosimetric effect later in the same treatment if the gantry is rotated by 90 degrees.

Also, for dynamic tracking of target, there may be no conformity check in place. Instead, the single axis tolerances are widened up to disable the axis limits to thereby allow for aperture adaptation (i.e., modifying positions of the MLC leaves to adapt to the target movement, or moving a patient support to place the target in alignment with the aperture of the collimator where the beam is exiting therethrough). Tracking conformity is then quantified for the end-to-end system test using volumetric phantoms. However, quantification of tracking conformity using volumetric phantoms is limited to simulated motion patterns, and is not available during treatment of real patient. Also, the above technique of widening up single axis tolerances may be hazardous to the patient, and may hinder clinical implementation of dynamic tracking protocols.

SUMMARY

A method for quantifying radiation beam conformity includes: obtaining first information regarding a prescribed aperture; obtaining second information regarding an actual aperture defined by components of a collimator (e.g., leaves of MLC collimator, blocks, jaws, etc.); and determining, using a processing unit, a metric based on the first information regarding the prescribed aperture and the second information regarding the actual aperture, wherein the metric indicates an amount of over-exposed aperture area, an amount of under-exposed aperture area, or both, and wherein the processing unit comprises one or more input for receiving the first and second information, and comprises a metric determination module configured to determine the metric based on the first information and the second information.

Optionally, the act of determining the metric comprises determining an overlapping area between the prescribed aperture and the actual aperture.

Optionally, the amount of over-exposed aperture area is based on a difference between the overlapping area and an area of the actual aperture, and the amount of under-exposed aperture area is based on a difference between the overlapping area and the prescribed aperture.

Optionally, the method further includes determining a measure of a target coverage by dividing the overlapping area by an area of the actual aperture.

Optionally, the metric determination module is configured to determine another metric based on current dose rate, tracking index, a treatment parameter, or any combination of the foregoing.

Optionally, the metric indicates whether the components (e.g., MLC leaves) of the collimator or a motion of a patient support, can keep up with a motion of a target.

Optionally, the act of determining the metric is performed during a treatment session.

Optionally, the act of determining the metric is performed between deliveries of radiation beams.

Optionally, the act of determining the metric is performed during a simulation, a quality assurance process, or a research process.

Optionally, the collimator is a part of a treatment system or a simulator.

Optionally, the act of determining the metric is performed in a treatment session in which a movement of a target region in a patient is tracked.

Optionally, the method further includes presenting the metric in a display.

Optionally, the method further includes determining whether to hold a delivery of a radiation based on the determined metric.

Optionally, if the metric indicates that a tolerance is exceeded, then the delivery of the radiation is held.

An apparatus for quantifying radiation beam conformity includes: a processing unit having one or more inputs; wherein the one or more inputs are for obtaining first information regarding a prescribed aperture, and second information regarding an actual aperture defined by components of a collimator; and wherein the processing unit comprises a metric determination module configured to determine a metric based on the first information regarding the prescribed aperture and the second information regarding the actual aperture, wherein the metric indicates an amount of over-exposed aperture area, an amount of under-exposed aperture area, or both.

Optionally, the processing unit further comprises an overlapping area determination module configured for determining an overlapping area between the prescribed aperture and the actual aperture.

Optionally, the amount of over-exposed aperture area is based on a difference between the overlapping area and an area of the actual aperture, and the amount of under-exposed aperture area is based on a difference between the overlapping area and the prescribed aperture.

Optionally, the processing unit further comprises a target coverage determination module configured for determining a measure of a target coverage by dividing the overlapping area by an area of the actual aperture.

Optionally, the metric determination module is configured to determine another metric based on current dose rate, tracking index, a treatment parameter, or any combination of the foregoing.

Optionally, the metric indicates whether the components (e.g., MLC leaves) of the collimator, or a motion of a patient support, can keep up with a motion of a target.

Optionally, the processing unit is configured for determining the metric between deliveries of radiation beams.

Optionally, the collimator is a part of a treatment system or a simulator.

Optionally, the actual aperture of the collimator is tracking a movement of a target region in a patient.

Optionally, the processing unit comprises an output for outputting the metric for presentation in a display.

Optionally, the apparatus further includes a control unit configured for determining whether to hold a delivery of a radiation based on the determined metric.

Optionally, the control unit is configured to hold the delivery of the radiation if the metric indicates that a tolerance is exceeded.

A processor-program product includes a set of instruction, an execution of which by a processing unit causes a method for quantifying radiation beam conformity to be performed, the method comprising: obtaining first information regarding a prescribed aperture; obtaining second information regarding an actual aperture defined by components of a collimator; and determining, using the processing unit, a metric based on the first information regarding the prescribed aperture and the second information regarding the actual aperture, wherein the metric indicates an amount of over-exposed aperture area, an amount of under-exposed aperture area, or both, and wherein the processing unit comprises one or more input for receiving the first and second information, and comprises a metric determination module configured to determine the metric based on the first information and the second information.

A method for quantifying radiation beam conformity includes: obtaining first information regarding a planned treatment; obtaining second information regarding an actual treatment; and determining, using a processing unit, a metric based on the first information regarding the planned treatment and the second information regarding the actual treatment, wherein the metric indicates an amount of radiation over-exposure, an amount of radiation under-exposure, or both, and wherein the processing unit comprises one or more input for receiving the first and second information, and comprises a metric determination module configured to determine the metric based on the first information and the second information.

Optionally, the planned treatment comprises a planned exposure of target, a planned exposure of organ-at-risks, or both.

Optionally, the amount of radiation over-exposure is quantified as a volume.

Optionally, the planned treatment comprises a prescribed aperture to be achieved by a collimator.

Optionally, the amount of radiation over-exposure is quantified as an amount of over-exposed aperture area.

Optionally, the metric indicates whether components (e.g., MLC leaves) of a collimator, or a motion of a patient support, can keep up with a motion of a target.

Optionally, the act of determining the metric is performed during a treatment session, a simulation, a quality assurance process, or a research process.

Optionally, the act of determining the metric is performed in a treatment session in which a movement of a target region in a patient is tracked.

Optionally, the method further includes determining whether to hold a delivery of a radiation based on the determined metric.

An apparatus for quantifying radiation beam conformity includes: a processing unit having one or more inputs; wherein the one or more inputs are for obtaining first information regarding a planned treatment, and second information regarding an actual treatment; and wherein the processing unit comprises a metric determination module configured to determine a metric based on the first information regarding the planned treatment and the second information regarding the actual treatment, wherein the metric indicates an amount of radiation over-exposure, an amount of radiation under-exposure, or both.

A processor-program product includes a set of instruction, an execution of which by a processing unit causes a method for quantifying radiation beam conformity to be performed, the method comprising: obtaining first information regarding a planned treatment; obtaining second information regarding an actual treatment; and determining, using the processing unit, a metric based on the first information regarding the planned treatment and the second information regarding the actual treatment, wherein the metric indicates an amount of radiation over-exposure, an amount of radiation under-exposure, or both, and wherein the processing unit comprises one or more input for receiving the first and second information, and comprises a metric determination module configured to determine the metric based on the first information and the second information.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION

Figure 1:
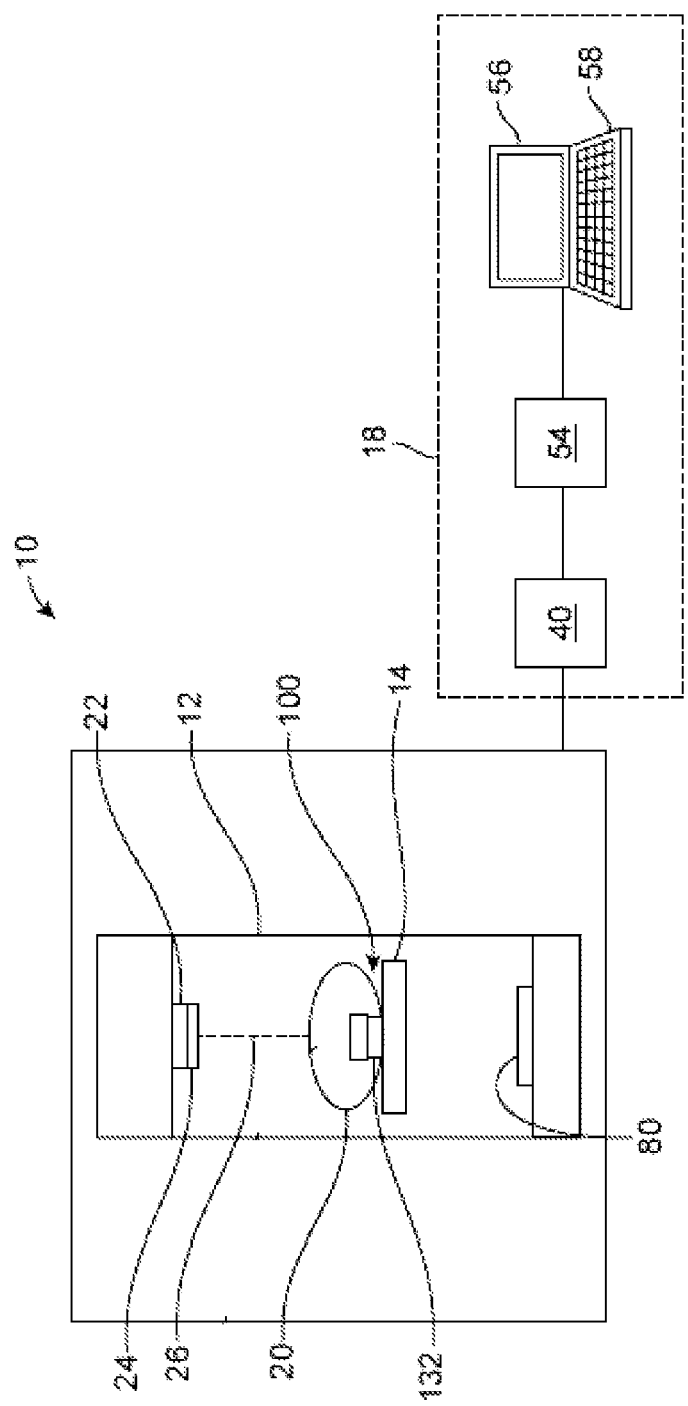
FIG. 1 illustrates a radiation treatment system.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates a radiation treatment system 10. The system 10 includes an arm gantry 12, a patient support 14 for supporting a patient 20, and a control system 18 for controlling an operation of the gantry 12 and delivery of radiation. The system 10 also includes a radiation source 22 that projects a beam 26 of radiation towards the patient 20 while the patient 20 is supported on support 14, and a collimator system 24 for changing and/or defining a cross sectional shape of the radiation beam 26. As used in this specification, the term "collimator" may refer to any device that has a radiation blocking capability, such as a multi-leaves collimator, a jaw assembly, a block, etc. Accordingly, a component of a collimator may be a leaf, a part of a jaw, or a part of a block, etc. The radiation source 22 may be configured to generate a cone beam, a fan beam, or other types of radiation beams in different embodiments. Also, in other embodiments, the source 22 may be configured to generate proton beam as a form of radiation for treatment purpose. Also, in other embodiments, the system 10 may have other form and/or configuration. For example, in other embodiments, instead of an arm gantry 12, the system 10 may have a ring gantry 12.

In the illustrated embodiments, the radiation source 22 is a treatment radiation source for providing treatment energy. In other embodiments, in addition to being a treatment radiation source, the radiation source 22 can also be a diagnostic radiation source for providing diagnostic energy for imaging purpose. In such cases, the system 10 will include an imager, such as the imager 80, located at an operative position relative to the source 22 (e.g., under the support 14). In further embodiments, the radiation source 22 may be a treatment radiation source for providing treatment energy, wherein the treatment energy may be used to obtain images. In such cases, in order to obtain imaging using treatment energies, the imager 80 is configured to generate images in response to radiation having treatment energies (e.g., MV imager). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 22 is able to generate X-ray radiation at a plurality of photon energy levels within a range anywhere between approximately 10 keV and approximately 20 MeV. In the illustrated embodiments, the radiation source 22 is carried by the arm gantry 12. Alternatively, the radiation source 22 may be located within a bore (e.g., coupled to a ring gantry).

In the illustrated embodiments, the control system 18 includes a processing unit 54, such as a processor, coupled to a control 40. The control system 18 may also include a monitor 56 for displaying data and an input device 58, such as a keyboard or a mouse, for inputting data. The operation of the radiation source 22 and the gantry 12 are controlled by the control 40, which provides power and timing signals to the radiation source 22, and controls a rotational speed and position of the gantry 12, based on signals received from the processing unit 54. Although the control 40 is shown as a separate component from the gantry 12 and the processing unit 54, in alternative embodiments, the control 40 can be a part of the gantry 12 or the processing unit 54.

In some embodiments, the system 10 may be a treatment system configured to deliver treatment radiation beam towards the patient 20 at different gantry angles. During a treatment procedure, the source 22 rotates around the patient 20 and delivers treatment radiation beam from different gantry angles towards the patient 20. While the source 22 is at different gantry angles, the collimator 24 is operated to change the shape of the beam to correspond with a shape of the target tissue structure. For example, the collimator 24 may be operated so that the shape of the beam is similar to a cross sectional shape of the target tissue structure. In another example, the collimator 24 may be operated so that different portions of the target tissue structure receive different amount of radiation (as in an IMRT procedure).

Figure 2:
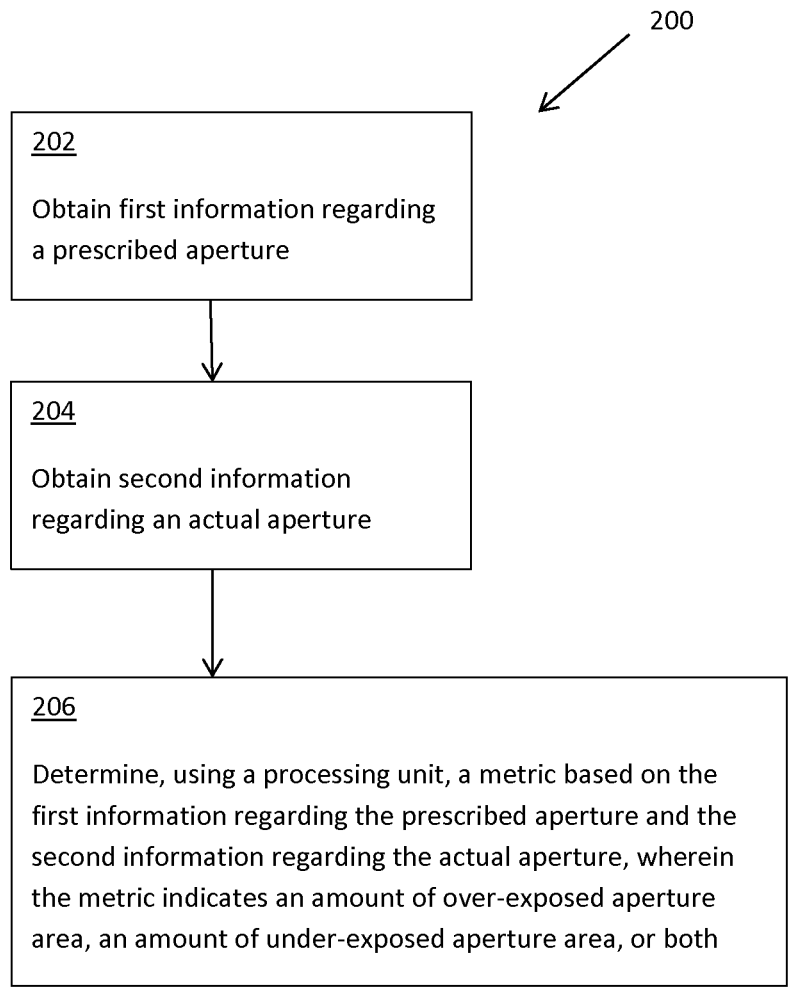
FIG. 2 illustrates a method for quantifying radiation beam conformity.

FIG. 2 illustrates a method 200 for quantifying radiation beam conformity in accordance with some embodiments. In some embodiments, the method 200 may be performed by a processing unit. By means of non-limiting examples, the processing unit may be the processing unit 54, or another processing unit. Also, the processing unit may be implemented using one or more processors, such as a FPGA processor, an ASIC processor, a microprocessor, a signal processor, a general purpose processor, or any of other types of processor. In some cases, the processing unit may be considered an improved processing unit compared to known processing units because the processing unit described herein contains features, functions, and/or capabilities that are believed to be unavailable in known processing units.

First, the processing unit obtains first information regarding a prescribed aperture (item 202). In some cases, the first information regarding a prescribed aperture may be a shape of a prescribed aperture, prescribed positions of leaves of the collimator for a prescribed aperture, any information that can be used to derive the shape of the prescribed aperture and/or the prescribed positions, any information that is derived from the shape of the prescribed aperture or from the prescribed positions of the leaves, or any combination of the foregoing. In one implementation, the first information may be an image representing a shape of a prescribed aperture. The image may be computer generated.

Next, the processing unit obtains second information regarding an actual aperture defined by components of a collimator (item 204). By means of non-limiting examples, the components of the collimator may be leaves of a MLC collimator, blocks of a collimator, jaws, etc. Also, collimator may be any device that is capable of blocking at least some radiation. In some cases, the second information regarding the actual aperture may be a shape of an actual aperture defined by leaves of the collimator, positions of leaves of the collimator defining the actual aperture, any information that can be used to derive the shape of the actual aperture and/or the actual positions of the leaves, any information that is derived from the shape of the actual aperture or from the actual positions of the leaves, or any combination of the foregoing. In one implementation, the second information may be an image indicating a shape of the actual aperture. In some embodiments, the image may be generated by activating the radiation source 22 while the collimator 24 is in a certain configuration (i.e., the leaves are in certain positions). The detector 80 receives the radiation and generates an image in response to the received radiation. The image provided by the detector 80 will have features indicating the shape of the aperture of the collimator 24. In other embodiments, the image indicating the shape of the actual aperture may be generated by a processor. For example, leaves positions of the collimator 24 may be processed by the processing unit, which creates an image of the aperture using the leaves positions.

Next, the processing unit determines a metric based on the first information regarding the prescribed aperture and the second information regarding the actual aperture (item 206). In some embodiments, the processing unit may include one or more input for receiving the first and second information, and comprises a metric determination module configured to determine the metric based on the first information and the second information. The metric indicates an amount of over-exposed aperture area, an amount of under-exposed aperture area, or both.

In some embodiments, the act of determining the metric in item 206 may include determining an overlapping area between the prescribed aperture and the actual aperture. For example, the processing unit may include an overlapping area determination module configured to determine the overlapping area between the prescribed aperture and the actual aperture. Also, in some embodiments, the processing unit may determine the amount of over-exposed aperture area by determining a difference between the overlapping area and an area of the actual aperture, and the amount of under-exposed aperture area by determining a difference between the overlapping area and the prescribed aperture.

In some embodiments, the determined metric may indicate an amount and/or shape of the under-exposed region, an amount and/or shape of the over-exposed region, an amount and/or shape of the overlapping region, or any combination of the foregoing.

In some cases, the aperture may be one that is defined with respect to the patient. For example, if the patient moves, the actual aperture (e.g., the collimation aperture may be projected to the actual patient position (e.g., a reference point in the patient) so that it moves with the patient. In some embodiments, the metric described herein may be used to capture patient movements by associating (e.g., coupling) the actual aperture to the actual patient position, and associating (e.g., coupling) the prescribed aperture to the prescribed patient position.

Figure 3B:
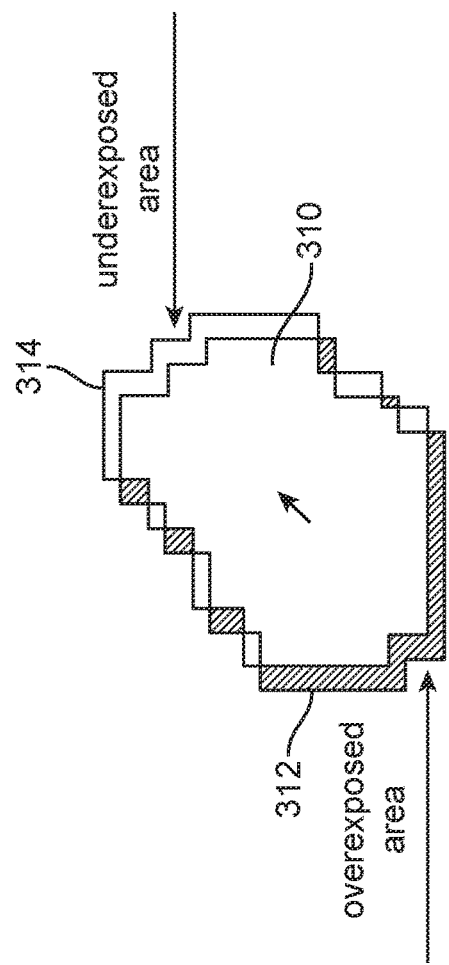
FIGS. 3A-3B illustrate a technique for quantifying radiation beam conformity.
Figure 3A:
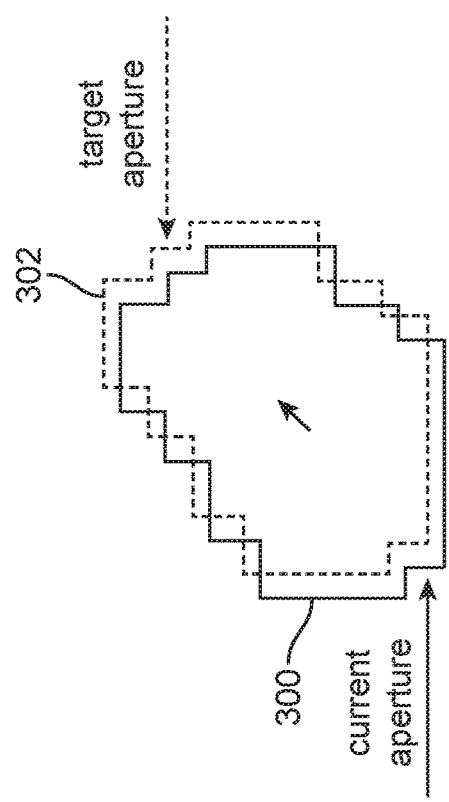

FIGS. 3A-3B illustrate the concept of over-exposed area and under-exposed area, which may be indicated by the determined metric. In FIG. 3A, the solid line 300 represents the shape of the actual aperture, and the dashed line 302 represents the shape or a target/prescribed aperture. As illustrated in the figure, during treatment, the actual aperture may not aligned with the prescribe aperture. In some embodiments, during item 206, the processing unit may determine the overlapping area 310 between the area of the actual aperture and the area of the prescribed aperture (FIG. 3B). The processing unit may also determine an amount and/or shape of the over-exposed region 312. In one implementation, the amount of the over-exposed region 312 may be calculated by the processing unit as the difference between the area of the actual aperture and the overlapping area 310. The processing unit may include an over-exposed region determination module configured to provide such function. Also, the processing unit may determine an amount and/or shape of the under-exposed region 314. In one implementation, the amount of the under-exposed region 314 may be calculated by the processing unit as the difference between the area of the prescribed aperture and the overlapping area 310. The processing unit may include an under-exposed region determination module configured to provide such function.

In some embodiments, the metric determined in item 206 may be a tracking index that functions as quality assurance (QA) measure to evaluate tracking accuracy. For example, the current aperture is translated by the beams eye view projected target vector. The area differences between the translated aperture (target aperture) and the current actual aperture are calculated as an overexposed area and an underexposed area. These values may be given in absolute area ($cm^2$), and/or as a percentage of the planned area (%). This quality assurance (QA) measure may be used for evaluating geometrical accuracy, which is applicable in all types of treatments.

In further embodiments, the method may further include determining a normalized version of the over-exposed area and the under-exposed area. Also, in some embodiments, the processing unit may be configured for determining a measure of a target coverage by dividing the overlapping area by a total area of the actual aperture. In one implementation, the processing unit may include a target coverage parameter determination module configured to divide the overlapping area by the area of the actual aperture. The resulting value may represent a degree of target coverage. See equation (1) below:

$$\text{Target coverage parameter (TCP)} = \text{overlapping area}/\text{area of actual aperture} \quad (1)$$

Also, the processing unit may be configured for determining a normal tissue parameter by dividing the overlapping area by an area of the planned aperture. In one implementation, the processing unit may include a normal tissue parameter determination module configured to divide the overlapping area by the area of the planned aperture. See equation (2) below:

$$\text{Normal tissue parameter (NTP)} = \text{overlapping area}/\text{planned aperture area} \quad (2)$$

It should be noted that the metric is not limited to the examples described, and that the metric may be determined based on other parameters. By means of non-limiting examples, the metric may be determined based on current dose rate (e.g., having unit of MU/sec), tracking index (e.g., having unit of $cm^2$), any of other parameters involved in treatment, or any combination of the foregoing. In some cases, the metric may be determined by multiplying a tracking index with the current dose rate. This provides an instantaneous flux deviation in $cm^2*MU/sec$.

In some embodiments, the metric indicates a degree of conformity. In other embodiments, the metric indicates whether the leaves of the collimator can keep up with a motion of a target.

In some cases, the act of determining the metric in item 206 may be performed during a treatment session. For example, the act of determining the metric may be performed between deliveries of radiation beams. In other embodiments, the treatment procedure may involve tracking a movement of a target region in a patient. In such cases, the act of determining the metric may be performed in a treatment session in which a movement of a target region in a patient is tracked. In the case of dynamic tracking, the prescribed aperture may include the planned (static) aperture, but adapted to the current target (e.g., shifted, rotated, scaled or otherwise deformed). This is because the target might not only move, but might also change its size dynamically (e.g., scaled, deformed, etc.). Then the prescribed aperture may change as well.

In other cases, the act of determining the metric in item 206 may be performed during a simulation, a quality assurance process, or a research process. Thus, the leaves contributing to the actual aperture in item 204 may be parts of a treatment system or a simulator.

In some embodiments, the method 200 may further include presenting the metric in a display. For example, the processing unit may forward the metric to a display for presentation to a user. The display may be a screen of a computer, a screen of an ipad, a screen of an iphone, a smart phone screen, a tablet screen, etc.

In some embodiments, instead of or in addition to presenting the metric to the display, the method may further include determining whether to hold a delivery of a radiation based on the determined metric. For example, the processing unit may include a beam-hold determination module configured to determine whether to hold a delivery of a radiation based on the metric. For example, if the metric indicates that a tolerance is exceeded, then the beam-hold determination module may determine that the delivery of the radiation is to be held. In such cases, the beam-hold determination module may then transmit a control signal to stop the delivery of the radiation. Thus, the determined metric may provide a tolerance check to determine if treatment is being delivered according to the treatment plan. In the case of dynamic tracking of a target, the beam is held while the conformity tolerance is exceeded (e.g., if the MLC leaves cannot keep up with a large target motion perpendicular to the leaf direction).

In some embodiments, the method 200 may further include determining an angular difference between a direction of an actual beam 26 shaped by the collimator 24, and a prescribed beam direction. For example, if a prescribed beam direction in a certain part of a treatment is 30 degrees, and if the actual beam direction is 32 degrees, then the angular difference will be 2 degrees in the example. The angular difference may be used as another measure of conformity between a prescribed treatment and an executed treatment. In some cases, for dynamic tracking, the prescribed direction of the beam may include the planned (static) direction, but adapted to the current target orientation (e.g., any rotation outside the collimation plane).

In some embodiments, the metric determined in item 206 may include one or more information. For example, in some embodiments, the metric may be a conformity measure that includes (1) over-exposed aperture area, (2) under-exposed aperture area, (3) a normalized version of the over-exposed aperture area, (4) a normalized version of the under-exposed aperture area, (5) angular difference between actual beam direction and prescribed beam direction, or (6) any combination of the foregoing.

In the above embodiments, the metric functions as a conformity measure that exploits the planned aperture. In other embodiments, the metric may be based on other planning data, such as target volume, or organs-at-risk volumes available as a three-dimensional structure set. Accordingly, over-exposure and under-exposure may be quantified as volumes.

Figure 4:
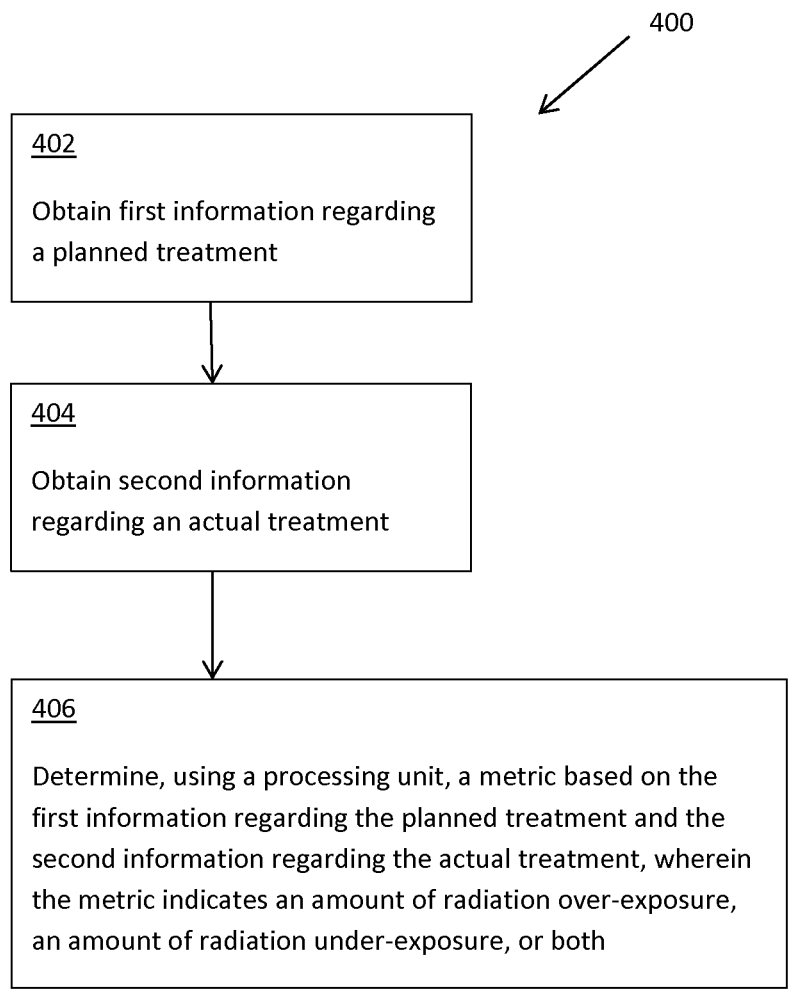
FIG. 4 illustrates another method for quantifying radiation beam conformity.

FIG. 4 illustrates another method 400 for quantifying radiation beam conformity in accordance with some embodiments. In some embodiments, the method 400 may be performed by a processing unit. By means of non-limiting examples, the processing unit may be the processing unit 54, or another processing unit. Also, the processing unit may be implemented using one or more processors, such as a FPGA processor, an ASIC processor, a microprocessor, a signal processor, a general purpose processor, or any of other types of processor. In some cases, the processing unit may be considered an improved processing unit compared to known processing units because the processing unit described herein contains features, functions, and/or capabilities that are believed to be unavailable in known processing units.

First, first information regarding a planned treatment is obtained by the processing unit (item 402). In some embodiments, the first information regarding a planned treatment may comprise information regarding a planned exposure of target, information regarding a planned exposure of organ-at-risks, or both. In some cases, the information regarding the planned exposure of target and organ-at-risks may be volumes available as a three-dimensional structure set.

In other embodiments, the first information regarding the planned treatment may comprise information regarding a prescribed aperture to be achieved by a collimator, as similarly discussed with reference to the method 200. For example, the first information regarding a planned treatment may be a shape of a prescribed aperture, prescribed positions of leaves of the collimator for a prescribed aperture, any information that can be used to derive the shape of the prescribed aperture and/or the prescribed positions, any information that is derived from the shape of the prescribed aperture or from the prescribed positions of the leaves, or any combination of the foregoing. In one implementation, the first information may be an image representing a shape of a prescribed aperture. The image may be computer generated.

Next, second information regarding an actual treatment is obtained by the processing unit (item 404). In some embodiments, the second information regarding the actual treatment may comprise information regarding an actual exposure of target, information regarding an actual exposure of organ-at-risks, or both. In some cases, the information regarding the actual exposure of target and organ-at-risks may be volumes constructed using radiation exposure data obtained during the treatment.

In other embodiments, as similarly discussed with reference to the method 200, the second information regarding the actual treatment may be a shape of an actual aperture defined by leaves of the collimator, positions of leaves of the collimator defining the actual aperture, any information that can be used to derive the shape of the actual aperture and/or the actual positions of the leaves, any information that is derived from the shape of the actual aperture or from the actual positions of the leaves, or any combination of the foregoing. In one implementation, the second information may be an image indicating a shape of the actual aperture. In some embodiments, the image may be generated by activating the radiation source 22 while the collimator 24 is in a certain configuration (i.e., the leaves are in certain positions). The detector 80 receives the radiation and generates an image in response to the received radiation. The image provided by the detector 80 will have features indicating the shape of the aperture of the collimator 24. In other embodiments, the image indicating the shape of the actual aperture may be generated by a processor. For example, leaves positions of the collimator 24 may be processed by the processing unit, which creates an image of the aperture using the leaves positions.

Next, the processing unit determines a metric based on the first information regarding the planned treatment and the second information regarding the actual treatment, wherein the metric indicates an amount of radiation over-exposure, an amount of radiation under-exposure, or both (item 406). In some cases, the processing unit may include one or more input for receiving the first and second information, and a metric determination module configured to determine the metric based on the first information and the second information.

In some embodiments, the act of determining the metric in item 406 may include determining an overlapping volume between the prescribed volume to be exposed to radiation and the actual volume of exposure. For example, the processing unit may include an overlapping volume determination module configured to determine the overlapping volume between the prescribed exposure volume and the actual exposure volume. Also, in some embodiments, the processing unit may determine the amount of over-exposed volume by determining a difference between the overlapping volume and a volume of the actual exposure, and the amount of under-exposed volume by determining a difference between the overlapping volume and the prescribed exposure volume.

Also, in some embodiments, different norms may be applied, in addition or instead of, the ones described previously. For example, the processing unit may quantify over-exposure and/or under-exposure in relation to the planned exposure of target and organ-at-risks.

In other embodiments, the metric may indicate an amount of over-exposed aperture area, an amount of under-exposed aperture area, or both, as similarly discussed with reference to method 200. For example, the amount of radiation over-exposure may be quantified as an amount of over-exposed aperture area, as similarly discussed with reference to method 200.

The act of determining the metric in item 406 may be performed during a treatment session, a simulation, a quality assurance process, or a research process. In some embodiments, the act of determining the metric in item 406 may be performed in a treatment session in which a movement of a target region in a patient is tracked.

Also, in some embodiments, the metric may indicate whether leaves of a collimator can keep up with a motion of a target.

In some embodiments, the method 400 may further include presenting the metric in a display. For example, the processing unit may forward the metric to a display for presentation to a user. The display may be a screen of a computer, a screen of an ipad, a screen of an iphone, a smart phone screen, a tablet screen, etc.

In some embodiments, instead of or in addition to presenting the metric to the display, the method 400 may further include determining whether to hold a delivery of a radiation based on the determined metric. For example, the processing unit may include a beam-hold determination module configured to determine whether to hold a delivery of a radiation based on the metric. For example, if the metric indicates that a tolerance is exceeded, then the beam-hold determination module may determine that the delivery of the radiation is to be held. In such cases, the beam-hold determination module may then transmit a control signal to stop the delivery of the radiation. Thus, the determined metric may provide a tolerance check to determine if treatment is being delivered according to the treatment plan. In the case of dynamic tracking of a target, the beam is held while the conformity tolerance is exceeded (e.g., if the MLC leaves cannot keep up with a large target motion perpendicular to the leaf direction).

It should be noted that the techniques for quantifying conformity described herein may be applicable for different types of treatments. For example, the conformity quantification techniques described herein may be used in the case of dynamic tracking, where the prescribed treatment plan may be modified during treatment to follow the movement of the target and/or organs at risk. In another example, the conformity quantification techniques described herein may also be used during treatment in which the treatment delivery is optimized for speed by smoothing out the transitions between linear axis position specified in the treatment plan.

Processing System Architecture

Figure 5:
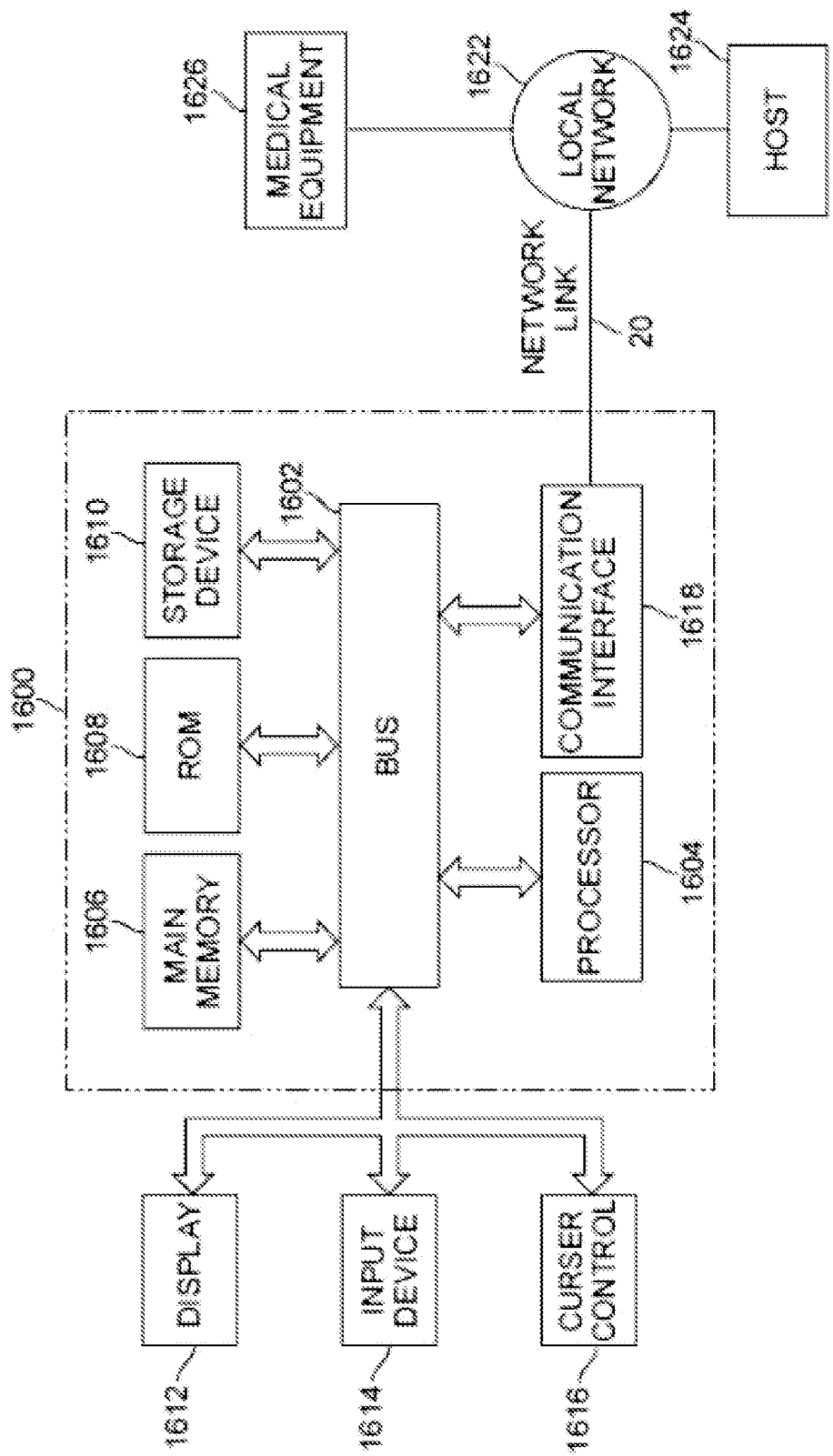
FIG. 5 illustrates a specialized processing system with which embodiments described herein may be implemented.

FIG. 5 is a block diagram illustrating an embodiment of a specialized processing system 1600 that can be used to implement various embodiments described herein. For example, the processing system 1600 may be configured to implement the method of FIG. 3 or the method of FIG. 4 in accordance with some embodiments. Also, in some embodiments, the processing system 1600 may be used to implement the processing unit 54 of FIG. 1. The processing system 1600 includes a bus 1602 or other communication mechanism for communicating information, and a processor 1604 coupled with the bus 1602 for processing information. The processor 1604 may be an example of the processor 54 of FIG. 1, or an example of any processor described herein. The processing system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processing system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processing system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processing system 1600 can be used to perform various functions described herein. According to some embodiments, such use is provided by processing system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the processing system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. A method for controlling radiation delivery, comprising:
   obtaining first information regarding a prescribed aperture, wherein the first information regarding the prescribed aperture comprises prescribed positions of collimator leaves, an aperture shape defined by the prescribed positions of the collimator leaves, data derived from the prescribed positions of the collimator leaves, data derived from the aperture shape, or any combination thereof;
   obtaining second information regarding an actual aperture created by the collimator leaves;
   determining, using a processing unit, a metric based on the first information regarding the prescribed aperture and the second information regarding the actual aperture, wherein the metric indicates an amount of over-exposed aperture area, an amount of under-exposed aperture area, or both, wherein the metric is a measure of a difference between the actual aperture created by the collimator leaves and the prescribed aperture defined by the prescribed positions of the collimator leaves, and wherein the processing unit comprises one or more input for receiving the first and second information, and comprises a metric determination module configured to determine the metric based on the first information and the second information; and
   controlling a delivery of radiation based at least in part on the metric that measures the difference between the actual aperture created by the collimator leaves and the prescribed aperture defined by the prescribed positions of the collimator;
   wherein the act of determining the metric comprises determining an overlapping area between the prescribed aperture and the actual aperture; and
   wherein the method further comprises determining a measure of a target coverage by dividing the overlapping area by an area of the actual aperture.

2. The method of claim 1, wherein the amount of over-exposed aperture area is based on a difference between the overlapping area and an area of the actual aperture, and the amount of under-exposed aperture area is based on a difference between the overlapping area and the prescribed aperture.

3. The method of claim 1, wherein the metric determination module is configured to determine another metric based on current dose rate, tracking index, a treatment parameter, or any combination thereof.

4. The method of claim 1, wherein the metric indicates whether the collimator leaves, or a motion of a patient support, can keep up with a motion of a target.

5. The method of claim 1, wherein the act of determining the metric is performed during a treatment session.

6. The method of claim 1, wherein the act of determining the metric is performed between deliveries of radiation beams.

7. The method of claim 1, wherein the act of determining the metric is performed during a simulation, a quality assurance process, or a research process.

8. The method of claim 1, wherein the collimator is a part of a treatment system or a simulator.

9. The method of claim 1, wherein the act of determining the metric is performed in a treatment session in which a movement of a target region in a patient is tracked.

10. The method of claim 1, further comprising presenting the metric in a display.

11. The method of claim 1, further comprising determining whether to hold a delivery of a radiation based on the determined metric.

12. The method of claim 11, wherein if the metric indicates that a tolerance is exceeded, then the delivery of the radiation is held.

13. An apparatus for performing the method of claim 1, comprising the processing unit,
wherein the processing unit comprises the metric determination module configured to determine the metric based on the first information regarding the prescribed aperture and the second information regarding the actual aperture.

14. The apparatus of claim 13, wherein the processing unit further comprises an overlapping area determination module configured for determining the overlapping area between the prescribed aperture and the actual aperture.

15. The apparatus of claim 13, wherein the processing unit further comprises a target coverage determination module configured for determining the measure of the target coverage by dividing the overlapping area by the area of the actual aperture.

16. The apparatus of claim 13, further comprising a control unit configured for determining whether to hold the delivery of the radiation based on the determined metric.

17. The apparatus of claim 16, wherein the control unit is configured to hold the delivery of the radiation if the metric indicates that a tolerance is exceeded.

18. A processor-program product having a set of instruction, an execution of which by the processing unit of claim 1 causes the method of claim 1 to be performed.

19. The method of claim 1, wherein the prescribed positions of the collimator leaves are determined by adjusting an initial set of planned positions of the collimator leaves based on a target shape.

20. A method for controlling radiation delivery, comprising:
obtaining first information regarding a prescribed aperture, wherein the first information regarding the prescribed aperture comprises prescribed positions of collimator leaves, an aperture shape defined by the prescribed positions of the collimator leaves, data derived from the prescribed positions of the collimator leaves, data derived from the aperture shape, or any combination thereof;
obtaining second information regarding an actual aperture created by the collimator leaves;
determining, using a processing unit, an overlapping area between the prescribed aperture and the actual aperture; and
determining a measure of a target coverage by dividing the overlapping area by an area of the actual aperture;
wherein the processing unit comprises one or more input for receiving the first and second information, and comprises a target coverage determination module configured to determine the measure of the target coverage; and
wherein the method further comprises controlling, by the processing unit, a delivery of radiation.

21. The method of claim 20, further comprising determining a metric, wherein the delivery of the radiation is controlled based on the metric.

22. The method of claim 21, wherein the metric is determined based on current dose rate, tracking index, a treatment parameter, or any combination thereof.

23. The method of claim 21, wherein the metric indicates whether the collimator leaves, or a motion of a patient support, can keep up with a motion of a target.

24. The method of claim 21, wherein the act of determining the metric is performed during a treatment session.

25. The method of claim 21, wherein the act of determining the metric is performed between deliveries of radiation beams.

26. The method of claim 21, wherein the act of determining the metric is performed during a simulation, a quality assurance process, or a research process.

27. The method of claim 21, further comprising determining whether to hold the delivery of the radiation based on the metric.

28. The method of claim 21, wherein the metric is a measure of a difference between the actual aperture created by the collimator leaves, and the prescribed aperture defined by the prescribed positions of the collimator leaves.

* * * * *